(12) United States Patent
Yamazaki

(10) Patent No.: US 6,834,097 B2
(45) Date of Patent: Dec. 21, 2004

(54) X-RAY CT APPARATUS AND X-RAY CT IMAGING METHOD

(75) Inventor: Masahiko Yamazaki, Tochigi-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/265,313

(22) Filed: Oct. 7, 2002

(65) Prior Publication Data
US 2003/0068005 A1 Apr. 10, 2003

(30) Foreign Application Priority Data
Oct. 5, 2001 (JP) ................................ P2001-309401

(51) Int. Cl.⁷ .............................................. G01N 23/00
(52) U.S. Cl. ................................................ 378/19; 378/4
(58) Field of Search ...................................... 378/4–20

(56) References Cited

U.S. PATENT DOCUMENTS 4,174,481 A * 11/1979 Liebetruth ................. 378/20
5,430,784 A * 7/1995 Ribner et al. ............. 378/19
5,612,985 A * 3/1997 Toki et al. .................. 378/4

FOREIGN PATENT DOCUMENTS

| JP | 61-82605 | 5/1986 |
| JP | 9-215687 | 8/1997 |
| JP | 11-76223 | 3/1999 |

* cited by examiner

Primary Examiner—Craig E. Church
(74) Attorney, Agent, or Firm—Oblon, Spivak, McClelland, Maier & Neustadt, P.C.

(57) ABSTRACT

An X-ray CT apparatus and method in which irradiated X-rays are effectively used, and the imaging of a wide-range scanogram can be conducted in a short time. The X-ray CT apparatus includes an X-ray tube for generating X-rays, an X-ray detector having a plurality of rows of X-ray detector elements arrayed in a slice thickness direction for detecting X-rays transmitted through a subject, a selector configured to select the row of the X-ray detector elements in the slice thickness direction necessary for generating a scanogram for a pre-set slice width, and a scanogram processing unit for generating the scanogram by using a data detected by the row of X-ray detector elements selected by the selector.

16 Claims, 12 Drawing Sheets

X-RAY CT APPARATUS AND X-RAY CT IMAGING METHOD

CROSS-REFERENCE TO RELATED APPLICATIONS

This application claims the benefit of priority from Japanese Patent Application No. 2001-309401, filed on Oct. 5, 2001, the entire contents of which are incorporated herein by reference.

BACKGROUND OF THE INVENTION

1. Field of the Invention

The present invention relates to an X-ray CT (Computed Tomography) apparatus, particularly to the imaging of a scanogram for positioning the photographing portion or setting the photographic condition, which is conducted preceding the CT image reconstruction process.

2. Description of the Background Art

Generally, a scanogram is an X-ray fluoroscopic image of a portion of a subject in a predetermined range of the subject. When imaging of the subject is conducted by an X-ray CT apparatus, a scanogram is initially obtained and on the basis of this scanogram, the positioning of the slice position or setting of the photographic condition is conducted. At this position, the scanning by the X-ray is then conducted and the CT tomogram is obtained.

For example, as disclosed in Japanese Utility Patent Disclosure (Kokai) 61-82605, the X-ray tube and X-ray detector are not rotated but held stationary. While the top board on which the subject is placed is being moved in the body axial direction of the subject, the X-ray is irradiated. On the basis of the obtained projection data, the scanogram is made.

When the scanning for obtaining the CT tomogram is conducted, the slice position is determined on the basis of the scanogram. Then, after the top board on which the subject is placed is returned to the initial position once, the top board is moved again and the x-ray tube is arranged at the slice position determined to the subject. While the X-ray tube is being rotated around the subject at each position, the X-ray irradiation is conducted. On the basis of the projection data obtained thereby, the tomographic image of the subject at each slice position is obtained.

The above described prior art X-ray CT apparatus is a single-slice CT apparatus. This single-slice CT apparatus has an X-ray tube irradiating a fan-shaped X-ray beam (fan beam), and an X-ray detector in which X-ray detector elements of the M channel (for example, 1000 channel) are arrayed fan-shaped or linearly in one row.

The prior art also includes an X-ray CT apparatus using a helical scan system. While the X-ray tube and the X-ray detector are continuously rotated in the prior art helical scan X-ray CT apparatus, the top board is made to move in the body axial direction (slice thickness direction) of the subject, and the tomographic data of the subject is acquired. Recently, a multi-slice CT apparatus is put to the practical use. The multi-slice CT apparatus has the X-ray tube irradiating the conical X-ray beam (cone beam), and the two dimensional X-ray detector having X-ray detector elements arrayed in slice thickness direction (in a body axial direction) in a plurality of rows, each X-ray detector element row having an array of M-channel elements (M channels times N rows).

In the imaging of the scanogram by the multi-slice CT apparatus, for example, as disclosed in Japanese Patent Disclosure (Kokai) 11-76223, the data output from the X-ray detector element of the X-ray detector is bundled in the row direction, and on the basis of the bundled data, the scanogram for 1 slice thickness (width) of the central position of the X-ray detector is generated.

However, in the imaging of the scanogram by the single slice CT apparatus, only the data for one slice width can be obtained by one imaging. Therefore, it takes a long period of time (for example, about 10 sec) in the imaging of the scanogram whose imaging range is wide. Accordingly, it takes a long period of time when using the scanogram to plan the scanning and, thus, therefore, there is a problem not only to force the burden on the subject (patient), but also to lower the patient throughput. Further, because the imaging is conducted by moving the subject for each slice thickness, an overlap is produced in adjoining slices at every time of the scanning, and there is a possibility to cause the subject to be irradiated with excess X-rays. Further, the time to irradiate the X-ray is prolonged, resulting in the shortening the life of the X-ray tube.

The same problem exists with the multi-slice CT apparatus because only 1 slice width data is obtained by 1 scanning. Thus, it takes a long period of time for the imaging of the scanogram of the necessary range. Therefore, the time to irradiate the X-ray is also undesirably prolonged.

SUMMARY OF THE INVENTION

In order to solve such problems, an object of the present invention is to use effectively the x-rays irradiated from the X-ray tube, and to conduct the imaging of a scanogram of wide range in a short time.

According to one aspect of the present invention, there is provided an X-ray CT apparatus including an X-ray tube for generating X-rays; an X-ray detector having a plurality of rows of X-ray detector elements arrayed in a slice thickness direction for detecting X-rays transmitted through a subject; a selector for selecting which of the rows of the X-ray detector elements in the slice thickness direction are necessary for generating a scanogram for a pre-set slice width; and a scanogram processing unit configured to generate the scanogram by using data detected by the row of X-ray detector elements selected by the selector.

According to another aspect of the present invention, there is provided a method of X-ray CT imaging including irradiating X-rays using an X-ray tube; detecting X-rays transmitted through a subject using an X-ray detector having a plurality of rows of X-ray detector elements arrayed in a slice thickness; selecting which of the rows of the X-ray detector elements in the slice thickness direction are necessary for generating a scanogram for a pre-set slice width; and generating the scanogram by using data detected by the selected row of X-ray detector elements.

According to the above-described structure, it is possible that wide range of the scanogram can be obtained in a short time, the burden to the subject is lightened, and the patient throughputs can also be increased.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENT

Figure 1:
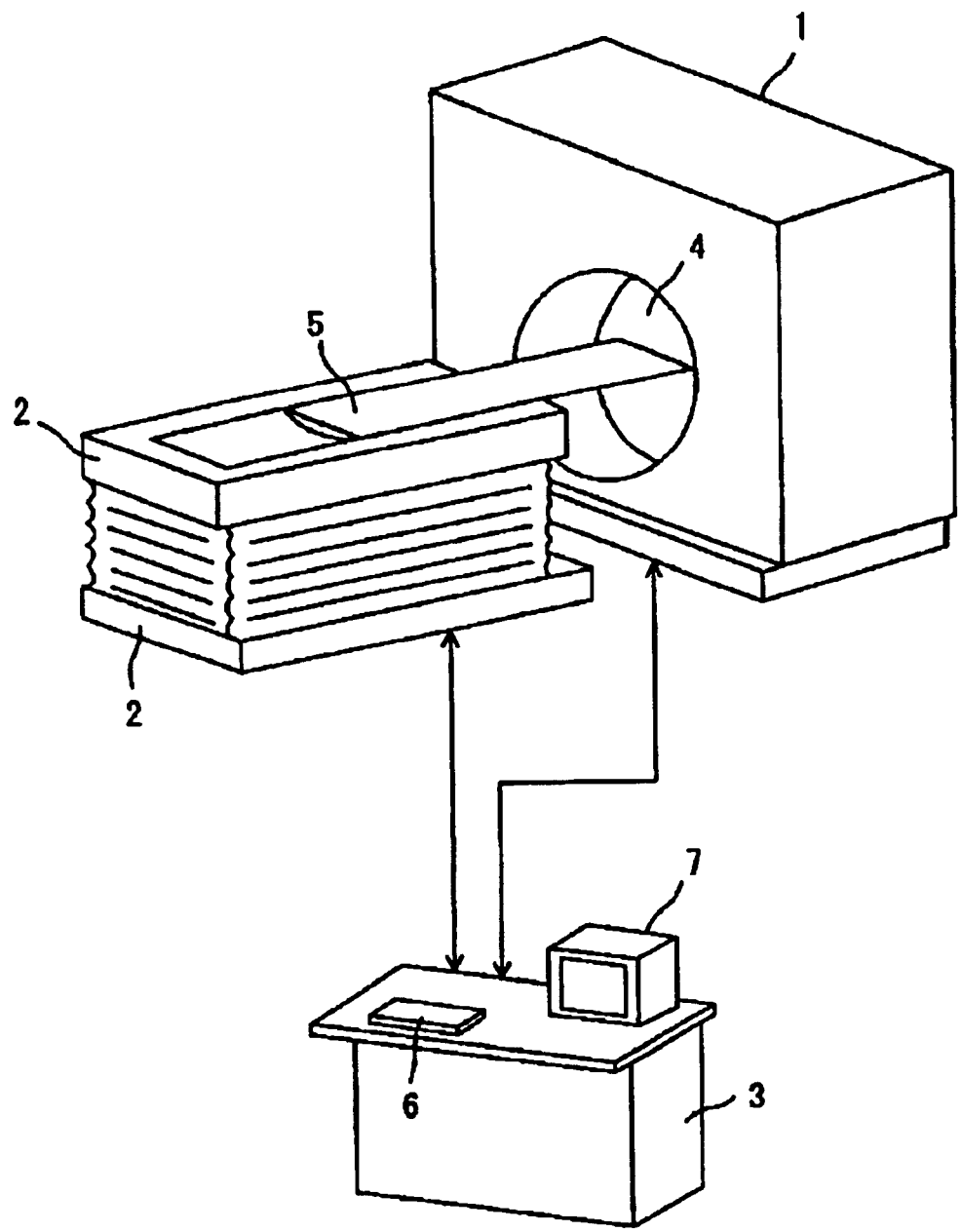
FIG. 1 is a schematic illustration of an X-ray CT apparatus according to an embodiment of the present invention.
Figure 2:
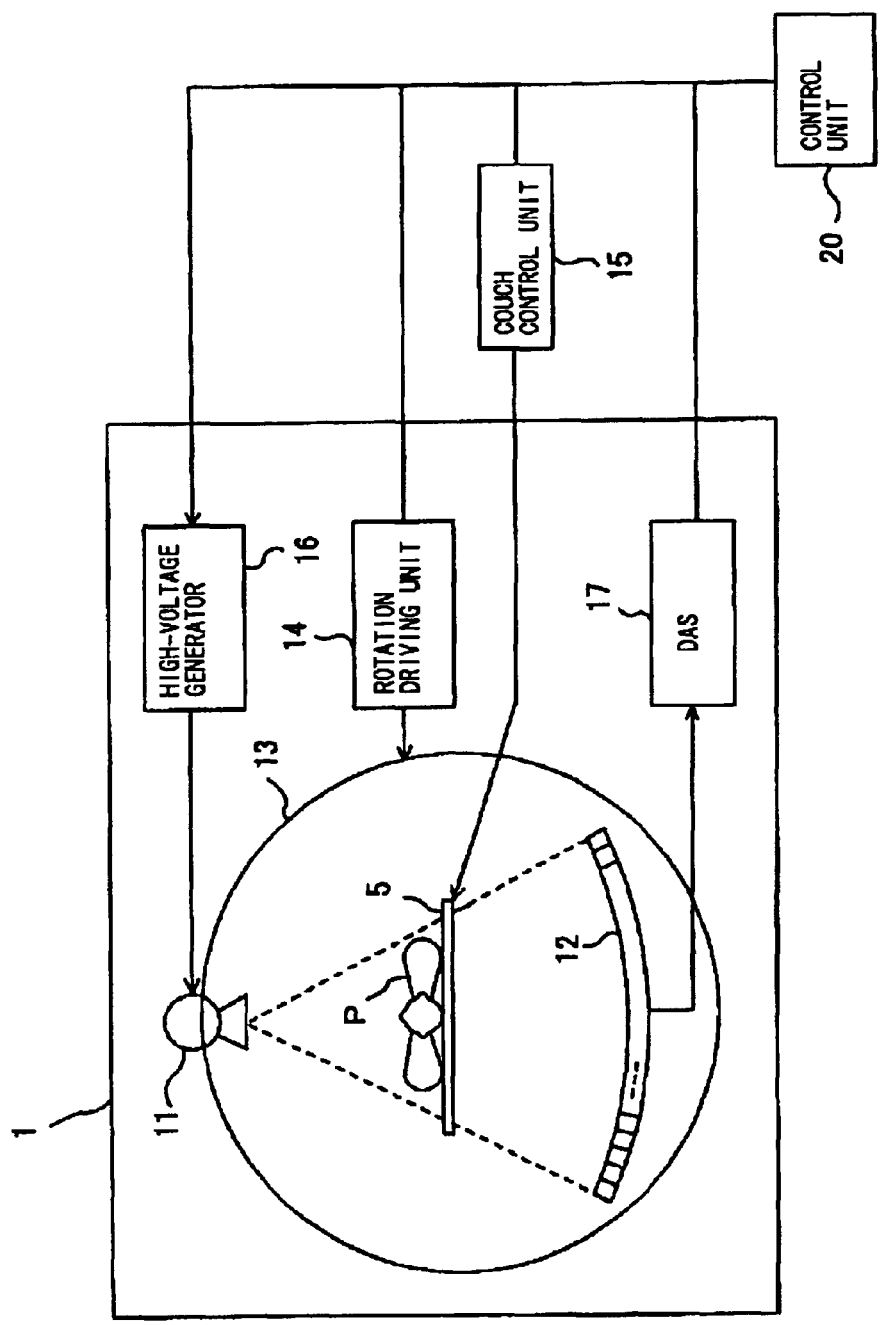
FIG. 2 is a block diagram of the X-ray CT apparatus according to an embodiment of the present invention.

Referring now to the diagram, where like reference numerals designate the same or corresponding parts throughout the several views, FIG. 1 is a schematic illustration of an X-ray CT apparatus according to an embodiment of the present invention, and FIG. 2 is a block diagram of the X-ray CT apparatus of FIG. 1.

This X-ray CT apparatus has a gantry 1, couch 2 arranged on the front surface of the gantry 1, and operating console 3 by which the gantry 1 and the couch 2 are operated and which controls each unit constituting the X-ray CT apparatus. On the upper surface of the couch 2, a top board 5 is provided upon which the subject can be placed and which can be moved in the body axial direction (slice width or thickness direction). The top board 5, on which the subject is placed, is slid to an aperture 4 of the gantry 1. In this condition, the adjustment of the height of the couch 2 and the movement (moving position and moving speed) of the top board can be controlled by the operation of the operating console 3. On the operating console 3, an input unit 6 having a pointing device such as a mouse or trackball, joystick, including a key board or CRT monitor 7 is arranged, and in the operating console 3, a control unit 20 which will be described later, is provided.

In the X-ray CT apparatus shown in FIG. 2, the gantry 1 supports an X-ray tube 11 and X-ray detector 12 by a rotation unit 13 in such a manner that they are opposite to each other with the subject placed on the top board 5 between them. The X-ray tube and the X-ray detector 12 can be continuously rotated around the subject. The drive of this rotation unit 13 is controlled by a rotation driving unit 14, and this rotation driving unit 14 controls the drive of the rotation unit 13 according to a driving control signal from a control unit 20. The X-ray tube 11 is connected to a high-voltage generator 16 through a slip ring. The high-voltage generator 16 supplies the tube current and the tube voltage to the X-ray tube 11 in a predetermined timing, according to an X-ray control signal from the control unit 20. In this manner, the conical X-ray beam (cone beam) is irradiated from the focus of the X-ray tube 11.

Further, a stop (collimator) is provided in the vicinity of an X-ray irradiation aperture in the gantry 1. The stop or collimator shapes the X-ray beam from the X-ray tube 11 into predetermined dimensions when a conical X-ray beam is irradiated onto the subject P. In this situation, the degree of the stop of X-ray beam can be controlled by the control unit 20.

Then, the X-ray transmitted the subject P is detected by the X-ray detector 12, which is connected to a data acquisition system (hereinafter, called DAS) 17 through the slip ring. This DAS 17 includes an integration unit to integrate the output from each X-ray detector element timely, and an A/D converter to convert the output of the integration unit into a digital signal. According to a data acquisition control signal from the control unit 20 supplied in the timing relating to the generation of the X-ray, the data from each X-ray detector element is acquired.

Further, a couch control unit 15 is connected to the couch 2. The couch control unit 15 can control the height of the couch 2 and the movement of the top board 5 according to a couch control signal from the control unit 20. For example, the top board 5 may be intermittently moved to a desired slice position by each predetermined amount, or may can be continuously moved ranging over a predetermined scan range. Further, the couch control unit 15 has a slide sensor for detecting the movement amount (slide amount) or the movement position (slide position) of the top board 5. The couch control unit 15 has a function to control the movement of the top board 5 according to the slide value (target value) from the control unit 20 and the present slide position detected by the slide sensor.

Figure 3:
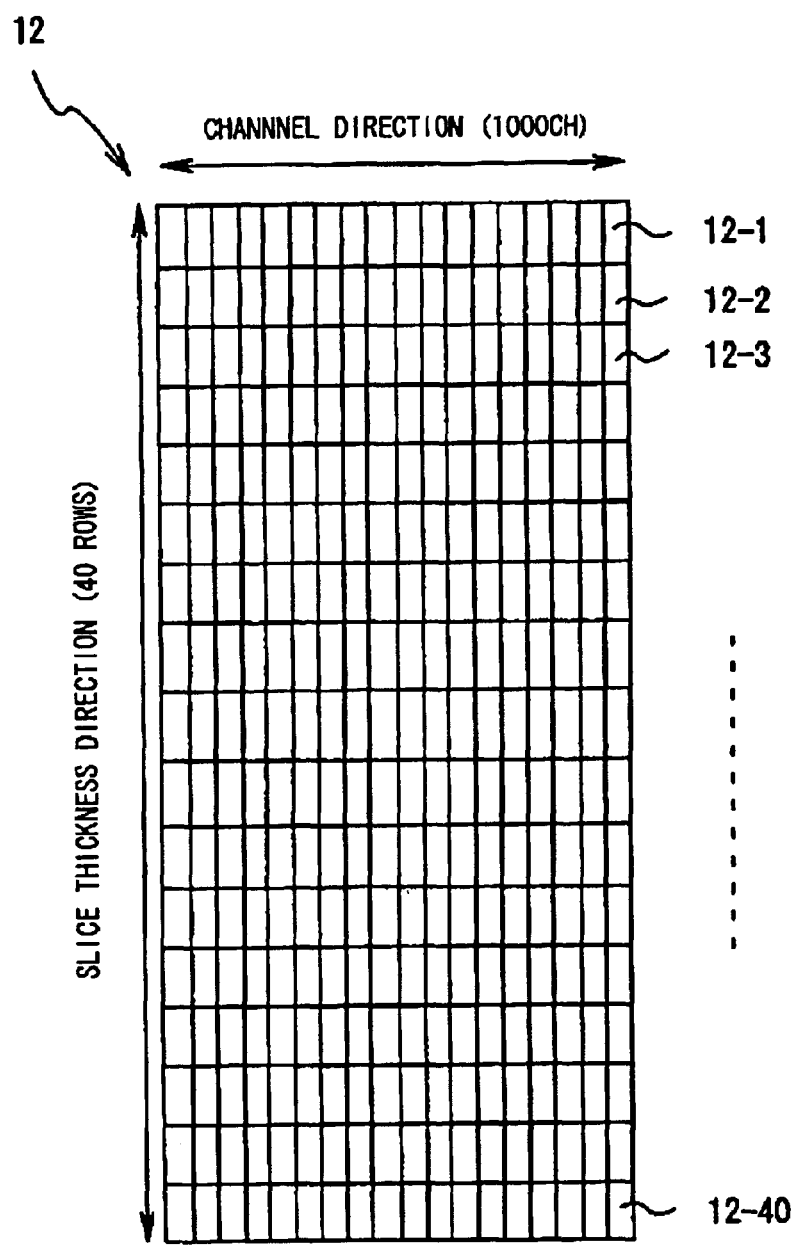
FIG. 3 is an illustration of the structure of an X-ray detector according to an embodiment of the present invention.

FIG. 3 is a view showing the outline structure of an X-ray detector 12 according to an embodiment of the invention. This X-ray detector 12 is structured as a 2 dimensional detector with an array of the X-ray detector elements. As shown in FIG. 3, there is a plurality of segments or elements (40 segs in the present embodiment) per 1 channel (the X-ray detector element column). The channel's elements are arranged in rows along the slice thickness direction (body axial direction). In this manner, the detector's elements are arranged array-like for the numbers of channels (1000 chs in the present embodiment) along the channel direction (ch direction). That is, the X-ray detector 12 in the present embodiment shown in FIG. 3 is a two-dimensional detector in which the X-ray detector elements are arranged matrix-like in 1000 chs over 40 rows. Further, a pitch of the X-ray detector elements in the slice thickness direction is for example 1 mm. This pitch is typically uniform from the central element to the element at the end portion (that is, the pitch of the array of the X-ray detector elements in rows 12-1–12-40 is 1 mm).

Figure 4:
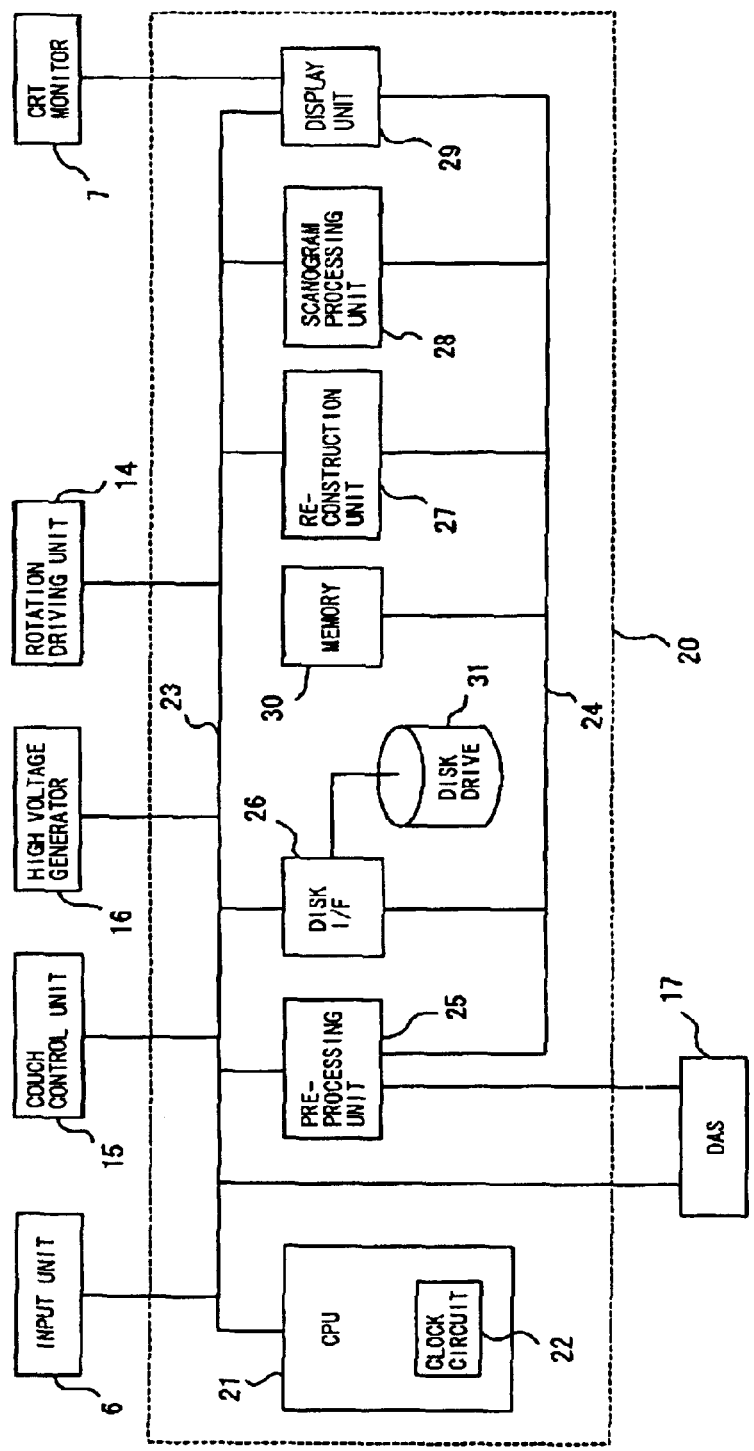
FIG. 4 is a block diagram of a control unit according to an embodiment of the present invention.

Next, the control unit 20 provided in the operating console 3 will be described with reference to FIG. 4. FIG. 4 is a block diagram showing the structure of the control unit 20 according to an embodiment of the invention. The control unit 20 performs central control of each unit of the X-ray CT apparatus, and has a CPU 21 as a host controller. This CPU 21 houses a clock circuit 22, and by using the clock from the clock circuit 22, the movement and time of each unit are controlled. The clock is supplied to each unit in the control unit as a common clock.

A control bus 23 and a data bus 24 are connected to the CPU 21. The CPU is also connected to pre-processing unit 25, disk interface 26, re-construction unit 27, scanogram processing unit 28 and display unit 29. Further, the pre-processing unit 25 and disk interface 26, reconstruction unit 27, scanogram processing unit 28, display unit 29 and memory 30 such as DRAM which can be read and written, are connected to the data bus 24. Then, a disk unit 31 as a large capacity memory unit is connected to the disk interface unit 26.

Further, previously, the slice width (an array of X-ray detector elements) for scano data processing is pre-set. When the scano data processing mode is selected (as requested by an operator), the array of X-ray detector elements for detecting the data of the pre-set slice width is selected, and according to the selection, the DAS determines the data to be acquired. In such a manner, only the data from the selected array of X-ray detector elements is acquired. Previously, one (for example, 4 rows) of a plurality of slice widths for the scano data processing may be set, or a plurality of slice widths (for example, 4 rows, 8 rows, 16 rows) may be set. When the operator designates the scano data processing, it may also be selected.

The control bus 23, the above-described input unit 6, rotation drive unit 14, couch control unit 15, high voltage generator 16, and DAS 17 are connected to the control unit 20 as outside structure. Further, the DAS 17 is connected to the pre-processing unit 25, and the CRT monitor 7 is connected to the display unit 29.

Figure 5:
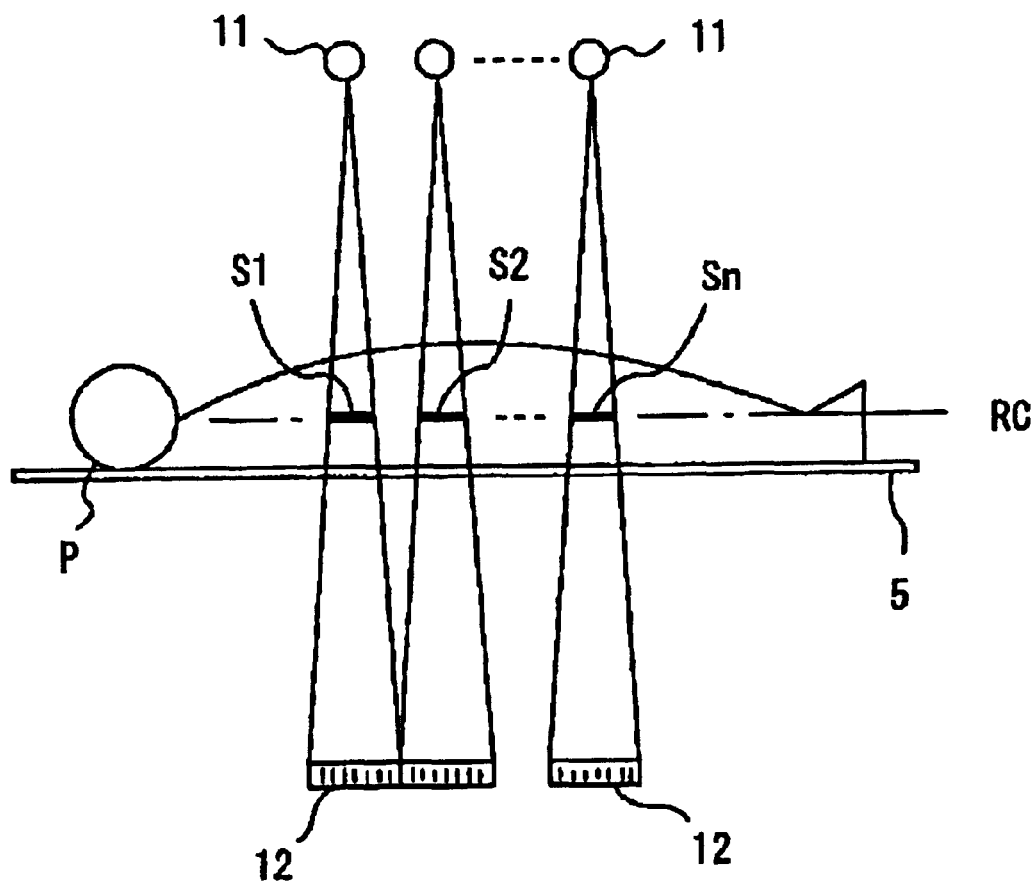
FIG. 5 is a schematic illustration of a situation of the scano data process in the first embodiment of the present invention.
Figure 6:
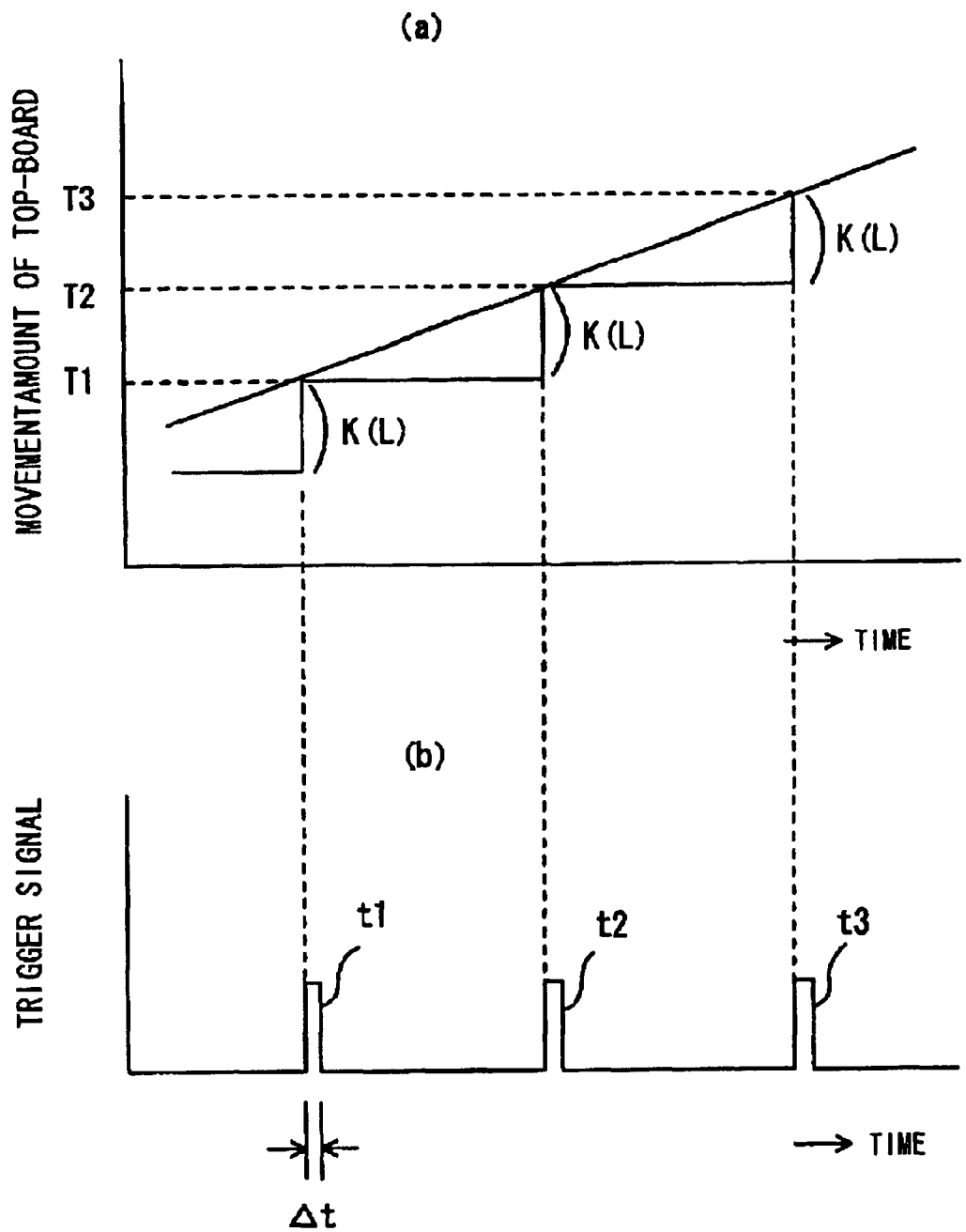
FIG. 6 is a graph and timing diagram showing the relationship between the movement of the top board and irradiation timing of the X-ray at the time of scano data process in an embodiment of the invention.

Further, the operation by the X-ray CT apparatus structured as described above, will be described below with reference to FIG. 5 and FIG. 6. FIG. 5 illustrates the scano data process in the first embodiment of the present invention. FIG. 6 illustrates the relationship between the movement of the top board and irradiation timing of the X-ray at the time of scano data process in an embodiment of the invention.

Initially, the operator designates the scano data process mode by the input unit 6. Then, the CPU 21 sends the control signal to the rotation driving unit 14 according to the previously set condition, and the rotation driving unit 14 arranges the X-ray tube 11 and X-ray detector 12. For example, as shown in FIG. 2, the X-ray tube 11 and X-ray detector 12 are arranged at the position which is horizontal to the top board 5 according to the control signal. Further, for the high voltage generator 16, values of the tube voltage and the tube current appropriate for the scano data process are respectively set.

Further, when the operator designates the movement of the top board 5 by the input unit 6, the CPU 21 sends the control signal to the couch control unit 15 corresponding to the designation. According to the control signal, the couch control unit 15 makes the top board 5 (on which the subject P is placed) slide to the start position of the scano data process. Further, the array of X-ray detector elements corresponding to the pre-set slice width is selected. Through the control unit 20, the CPU 21 controls the drive of DAS so that only DAS corresponding to the selected array (rows) of the X-ray detector elements acquires the data.

After preparation for the scano data process is completed, the scano data process is conducted. When the start of the scano data process is designated form the input unit 6, the CPU 21 sends the control signal to each unit corresponding to the designation. Initially, the X-ray of the dose for the scano data process is irradiated from the X-ray tube 11 to the subject P. The X-ray transmitted through the subject P is detected by the X-ray detector 12, converted into an electric signal corresponding to the transmitted X-ray amount, and outputted. This output is acquired by the DAS 17 as the X-ray transmission data. The data acquired by the DAS 17 is processed by the pre-processing (water correction) in the pre-processing unit 25, and the projection data after the pre-processing is temporarily stored in the memory 30 through the data bus 24 together with the position information of the scano data process to the subject P. The projection data is read out from the memory 30, and sent to the scanogram processing unit 12 and the scanogram data is generated.

The data of 40 slices can be obtained in the X-ray detector 12 because, in the X-ray detector 12, the array of X-ray detector elements of 40 rows are arranged in the body axial direction. However, in the present embodiment, the scanogram data for 40 slices is generated by using the data for 40 slices. That is, the data detected at the position of 12-1 in FIG. 3 is used as the data for generating the scanogram corresponding to that slice position.

As described above and shown in FIG. 5, the next scano data processing is conducted after the first scano data processing is conducted and the data in the range of S1 (40 slices) on the rotation central axis RC of the X-ray tube 11 and X-ray detector 12 is obtained. The next scano data processing is conducted by moving the top board 5 by the row width K of the X-ray detector 12 (that is, the width K which totaled all of the X-ray detector element rows (40 rows) arranged in the slice thickness direction of the X-ray detector 12). Then, the data of the next S2 range (40 slices) is obtained. In the same manner, the data up to the range Sn is obtained. In this situation, the beam width (each Si) in the body axial direction when the X-ray transmits the rotation central axis RC of the X-ray tube 11 and the X-ray detector 12 corresponds to the slice thickness in the scanogram. That is, by one time scan imaging, the projection data for the slice thickness Si can be obtained.

In this case, a portion not covered by the X-ray beam is generated because the subject P is successively moved by the distance equivalent to all of the X-ray element rows arranged in the slice thickness direction of the X-ray detector 12 (the width K of the X-ray detector 12) every X-ray irradiation. As shown in FIG. 5, the projection data does not exist between the obtained projection data (between Sn-1 and Sn). Therefore, when the scanogram is made, the missing data is filled in, for example, by interpolation of the before and after projection data. In this manner, the scanogram in the desired range is made.

After the data of the generated scanogram is temporarily stored in the display memory 29, it is displayed on the CRT monitor 7 as the scanogram. The data of this scanogram is separately read from the display memory 29, and stored in the disk drive 31 through the disk interface 26. The data is read out as needed and the scanogram can be displayed on the CRT monitor 7.

Next, the relationship between the position information of the top board 5 and the trigger signal of the X-ray irradiation from the X-ray tube 11 is explained with reference to FIG. 6. In FIG. 6(a), the horizontal axis shows the time and the vertical axis shows the movement amount of the top board 5 (that is, the irradiation position of the X-ray to the subject P). Further, FIG. 6(b) shows the timing of trigger signal generation when the X-rays are irradiated.

As can clearly be seen from this view, initially, the couch drive unit 15 moves the top board 5 so that the subject P is positioned at a predetermined start position T1 for the scano data process. Then, the CPU 21 gives the first trigger signal t1 to the high-voltage generator 16, the X-ray is irradiated from the X-ray tube 11, and the first scano data processing is conducted. The pulse width Δt of the trigger signal is, for example, about 0.1 sec. When the irradiation of the X-rays is stopped, the couch driving unit 15 slides the top board 5 in the slice width on thickness direction. Then, when the sliding amount reaches the row width of the X-ray detector 12, the CPU 21 gives the trigger signal t2 to the high-voltage generator 16 at the position T2, and the second scano data processing is conducted. Hereinafter, in the same manner, the X-rays are intermittently irradiated and the scano data processing in the desired range is conducted.

As described above, the irradiation timing of the X-rays is controlled according to the sliding amount of the top board. Therefore, the X-ray can be irradiated at the optimum timing so that the X-ray can be effectively used. As a result, a scano data process can be realized where excessive X-ray exposure to the subject is suppressed.

In this case, it is not necessary to irradiate the X-rays when the top board 5 is stopped. While the top board 5 is continuously slid, X-rays may be irradiated by generating the trigger signal every time when the top board 5 moves by a distance which totaled all of the X-ray element rows arranged in the slice thickness direction of the X-ray detector 12, or the X-ray may be irradiated continuously during the scano data process.

According to the scanogram obtained in this manner, a scan plan is made. According to the scan plan, the operator inputs the scan conditions from the input unit 6, and when the designation of the scan is conducted, the control signal according to the scan conditions is sent from the CPU 21 to each unit of the X-ray CT apparatus. The couch control unit 15 moves the top board 5 on which the subject P is placed, adjusting to the scan start position according to the scan plan. After that, the rotation driving unit 14 drives the rotation unit 13 at a predetermined speed (for example, 0.5 sec/1 rotation or 1 sec/1 rotation) and continuously rotates the X-ray tube 11 and X-ray detector 12 around the subject P. For that time, the high-voltage generator irradiates the X-rays from the X-ray tube 11, and the X-ray transmission data in many directions are acquired. Because the X-ray detector 12 is a two-dimensional detector, the data for a plurality of slices can be acquired every rotation. However, the acquisition of the data may be performed when moving the top board 5 or/and the gantry 1 continuously during the continuous rotation.

After the acquired data is pre-processed (such as the calibration in the pre-processing unit 25), it is temporarily stored in the memory 30 as the projection data (raw data) through the data bus 24 together with the position information expressing the position of the view of the subject P. The projection data is then sent to the re-construction unit 27 and the CT image reconstruction data are produced using the projection data. Herein, a "view" means a set of the projection data at a certain angle to the subject P. After the re-constructed CT image data are temporarily stored in the display unit 29, then the re-constructed CT image is displayed on the CRT monitor 7 as the tomographic image. The data of the tomographic image are separately read from the display unit 29, and stored in the disk drive 31 through the disk interface 26. These data are read out as needed and can be displayed on the CRT monitor 7 as the tomographic image.

According to embodiments of the present embodiment, a scanogram in the desired range can be obtained by the number of times of scano imaging not larger than the conventional one because the scano data of a plurality of slices can be acquired by a one time scano data process. In this way, the scano data process can be completed in a short time. Accordingly, the burden to the subject at the time of CT imaging can be lightened. Further, the array of X-ray detector elements (the X-ray detector element rows) necessary for generating the scanogram of the pre-set plurality of slice widths is selected and the scano data processing is conducted. The scanogram is then generated by using the data of the selected array of X-ray detector elements (the selected X-ray detector element row or rows). Therefore, the resolution of the generated scanogram is better than the conventional scanogram.

Next, a second embodiment of a scano data process of the present invention will be described with reference to FIG. 7. The structure of the X-ray CT apparatus according to the second embodiment is the same as the first embodiment. A difference of the second embodiment over the first embodiment is that the slide pitch of the top board which is moved every scano data process is a little smaller than the case of the first embodiment. Thus, the method, such as interpolation, for supplying the lack of the data at the time of making the scanogram is not necessary in this embodiment.

Figure 7:
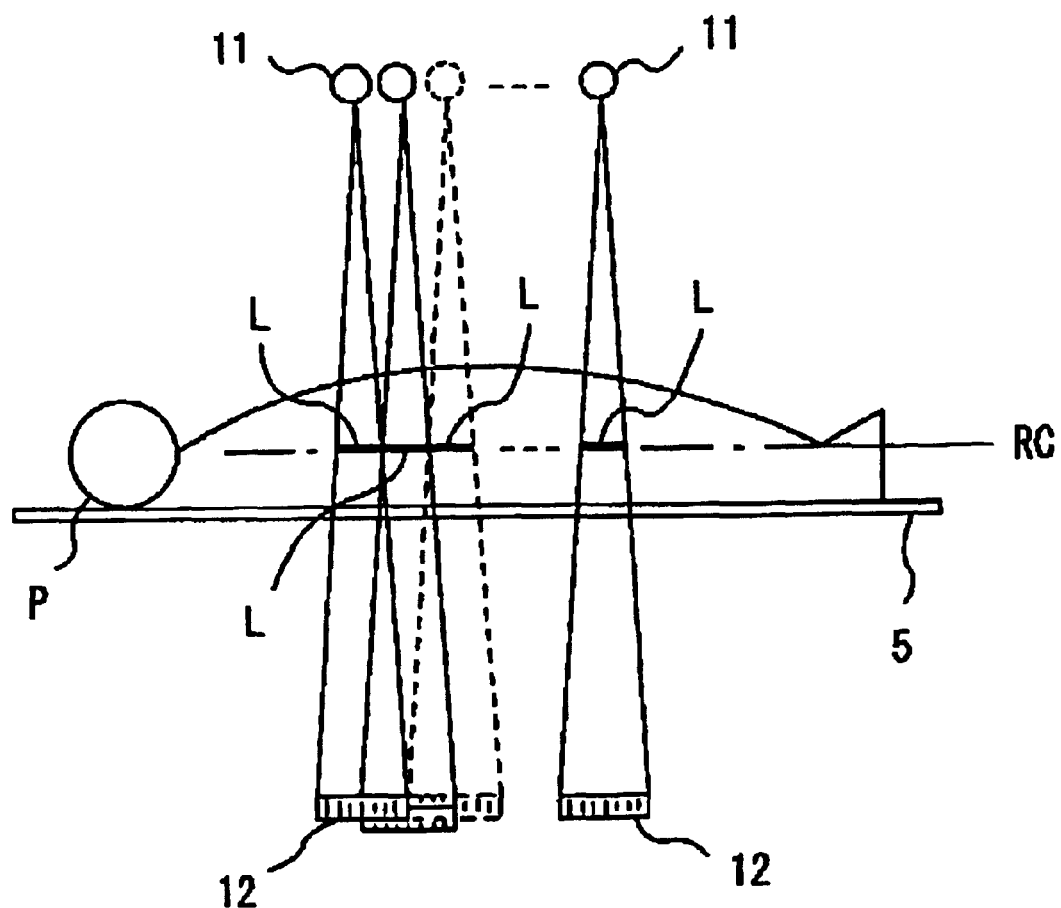
FIG. 7 is a schematic illustration of a scano data process in a second embodiment of the present invention.

As shown in FIG. 7, in the rotation central axis RC of the X-ray tube 11 and X-ray detector 12, the top board 5 is slid by a distance equivalent to the width L (4 slices) of X-ray beam width L on the RC at every scano data process. Thus, the scano data processing is conducted without missing or overlapping data, and so that the X-ray beam before and behind imaging may touch mutually in the slice thickness direction (body axial direction).

Also in the present embodiment, the relationship between the position information of the top board 5 and the trigger signal of the X-ray irradiation from the X-ray tube 11 is as shown in FIG. 6. That is, initially, after the first scano data processing is conducted at a predetermined start position T1, the top board 5 is slid in the slice thickness direction. Then, when its movement amount reaches the X-ray beam width L on the RC, the trigger signal is given to the high-voltage generator 16, and the second scan photographing is conducted. Hereinafter, in the same manner, the X-ray is intermittently irradiated, and the scan imaging in the desired range is conducted.

At the time, it is preferable that, corresponding to the pulse width of the irradiated X-ray (that is, the pulse width Δt of the trigger signal), the movement speed of the top board 5 is set to an optimum speed. The reason is that during the X-ray irradiation, when the subject P (that is, top board 5) is moved by the width of 1 row of the array of X-ray detector elements in the slice width direction in the X-ray detector 12 (for example, 10% or more), the overlap portion of the obtained scanogram becomes large, and the irradiated X-ray for that amount become useless.

Accordingly, in the case where the slice width on the RC is Δr, and the pulse width of the irradiated X-ray is Δt, an optimum moving speed, V is established as follows:

$$V \leq (0.1 \times \Delta r)/\Delta t \qquad (1)$$

when a value of V satisfying the above expression is set as the optimum moving speed of the top board 5, the overlap of the scanogram is small. Furthermore, compensation such as interpolation at the time of scanogram re-construction is not necessary, so the scanogram, which is not wasteful and is more accurate, can be obtained in a comparatively short time. Further, the array of the X-ray detector elements (the X-ray detector element rows) necessary for generating the scanogram of the pre-set plurality of slices are selected and the scano data processing is conducted. The scanogram is generated by using the data of the selected array of X-ray detector elements (the selected X-ray detector element row). Therefore, the resolution of the generated scanogram is better than the conventional scanogram.

In this situation, in the first and second embodiments, the scanogram is generated on the basis of the output data of all of array of X-ray detector elements (all of X-ray detector element rows) in the body axial direction in the X-ray detector 12 (that is, all of X-ray detector elements in the X-ray detector 12). It is preferable that the DAS 17 acquiring the output data, corresponding to the X-ray detector elements both in the channel direction and the slice direction, is composed of active elements including the same number of integrators or A/D converters. However, this is not required for all embodiments, when the mounting space to the gantry 1 or the cost performance is a limiting factor, the number of DAS 17 active elements which can be installed has a limitation. When the active elements of the same number as the X-ray detector elements are arranged in the channel direction, in the slice thickness direction, only the active element of about 10 rows at the most can be arranged. That is, to the X-ray detector 12, the number of DAS 17 devices which can be installed is at most ten.

Accordingly, the X-ray detector 12 and DAS 17 may be connected through a multiplexer composed of a switching element, so the output data from all of X-ray detector elements structured in the 2 dimensional array can be acquired even if the number of DAS 17 active elements is small.

Figure 8:
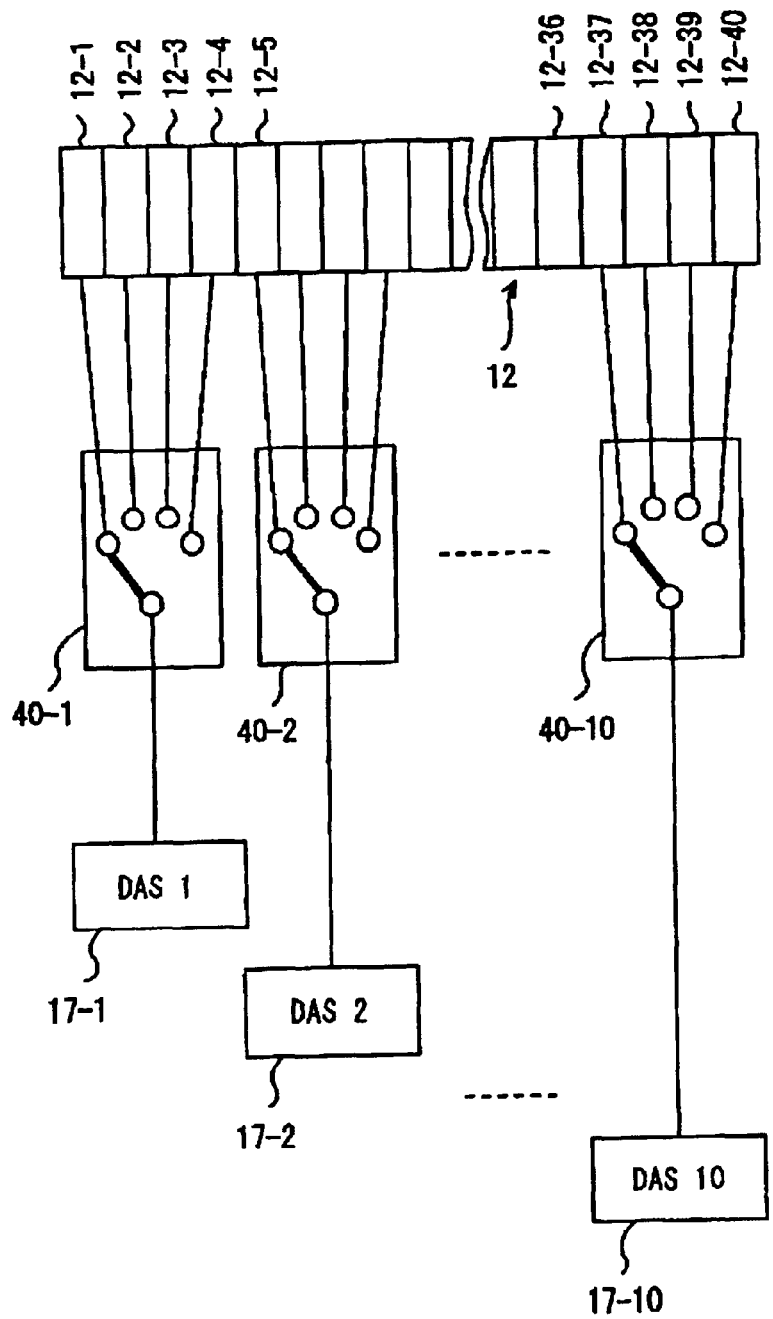
FIG. 8 is a schematic illustration of a multiplexer connecting the X-ray detector with the DAS according to an embodiment of the present invention.

FIG. 8 is a view showing the structure of the multiplexer connecting the X-ray detector with the DAS in an embodiment of the invention. For example, as shown in FIG. 8, in the case of the two-dimensional array-like detector in which the X-ray detector 12 is composed of 40 rows of array of X-ray detector elements (40 X-ray detector element rows) in the slice thickness direction, 10 DAS's 17 may be arranged with 10 multiplexers 40. Then, one multiplexer 40 is allotted for every 4 rows of X-ray detector elements in the slice thickness direction of the X-ray detector 12. The first multiplexer 40-1 is positioned between the X-ray detector elements from the first row (12-1) of the X-ray detector 12 to the fourth row (12-4) and the first DAS 17-1. Further, second multiplexer 40-2 is positioned between the X-ray detector elements from the fifth row (12-5) of the X-ray detector 12 to the eighth row (12-8) and the second DAS 17-2. Successively, in the same manner, the tenth multiplexer 40-10 is positioned between the X-ray detector element from the 37th row (12-37) to the 40th row (12-40) of the X-ray detector 12 and the tenth DAS 17-10.

Then, each of multiplexers 40-1 to 40-10 is synchronously operated such that the signal from each of 4 rows of X-ray detector elements of the X-ray detector 12 shared with respective multiplexers is successively switched and read out, and the read out signal is supplied to DAS's 17-1 to 17-10. That is, initially, the signal detected in the X-ray detector elements of the first row (12-1), fifth row (12-5), ninth row (12-9), 13th row (12-13), 17th row (12-17), 21th row (12-21), 25th row (12-25), 29th row (12-29), 33th row (12-33) and 37th row (12-37) of the X-ray detector 12 is supplied to DAS's 17-1 to 17-10, respectively. Next, the signal detected in the X-ray detector elements of the second row (12-2), sixth row (12-6), . . . 38th row (12-38) of the X-ray detector 12, is supplied to DAS's 17-1 to 17-10, respectively. Further, the signal detected in the X-ray detector elements of the third row (12-3), seventh row (12-7), . . . , 39th row (12-39) of the X-ray detector 12, is supplied to DAS's 17-1 to 17-10, respectively. Finally, the signal detected in the X-ray detector elements of the fourth row (12-4), eighth row (12-8), . . . , 40th row (12-40) of the X-ray detector 12, is supplied to DAS's 17-1 to 17-10, respectively. In this situation, the X-ray detector elements of the X-ray detector 12 store the electric charge while the signal is read out.

Then, the projection data for 40 slices is obtained by the first time X-ray irradiation. Next, the subject P is moved to the position to obtain the projection data for the next 40 slices, and the scanogram of this portion is generated during the time when the subject is moving, and displayed on the CRT monitor 7. Further, the scanogram for 40 slices is successively generated by the second and subsequent X-ray irradiation. The scanogram whose range is expanded for the part of the generated image is successively displayed on the CRT monitor 7, every time when the scanogram is generated. In the recent helical CT apparatus, following the helical scanning operation, the tomogram can be displayed in real time. However, one sheet of the tomographic image can be reconstructed in a shorter time than the acquisition time of the projection data necessary for reconstructing one sheet of the tomographic image. Accordingly, therefore by applying this technology, the scanogram is easily displayed in real time like a motion picture.

As described above, the X-ray detector 12 and the DAS 17 are connected with each other through the multiplexer so the output data from the all X-ray detector elements structured in the two-dimensional array-like detector can be acquired even if the number of the DAS 17 is small. Therefore, the number of the data acquisition apparatus is reduced and the mounting space can be reduced while meeting an intended increase of the cost for performance.

Figure 9:
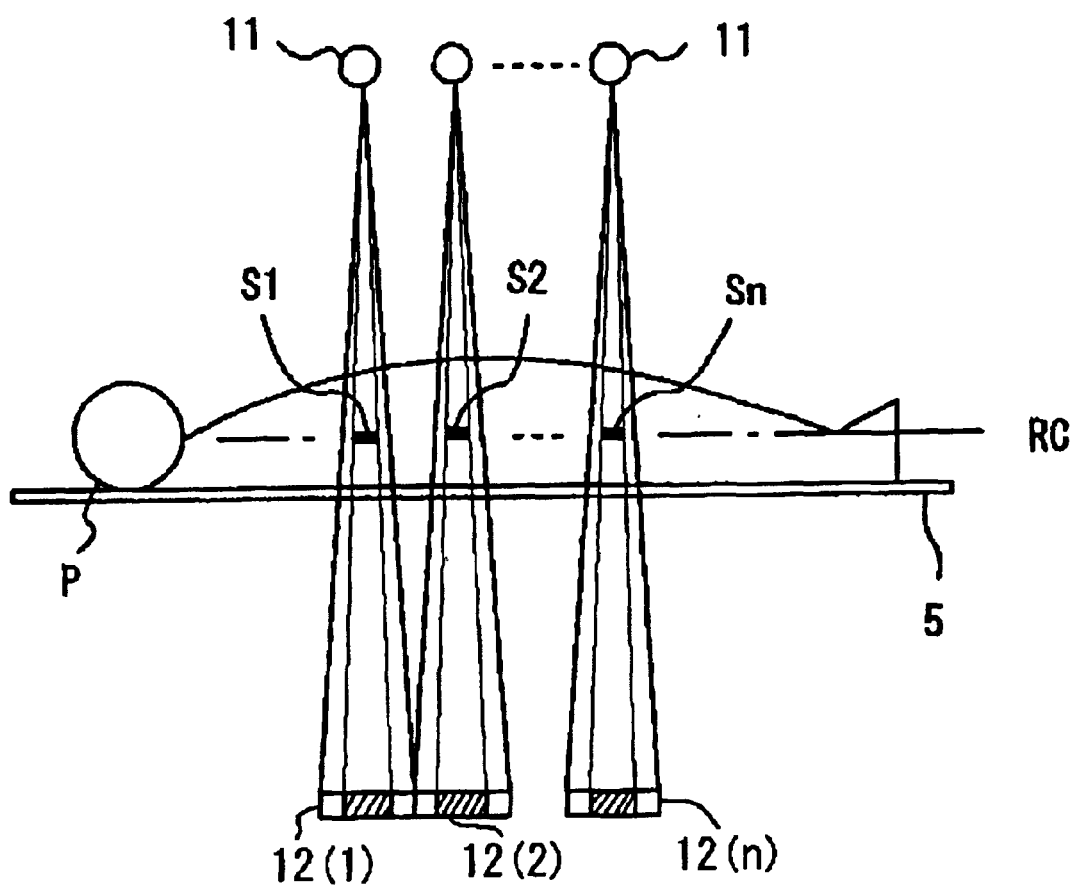
FIG. 9 is a schematic illustration of a scano data process in the third embodiment of the present invention.

Next, a third embodiment of the present invention will be described with reference to FIG. 9. In this situation, the structure of the X-ray CT apparatus is the same as in the above-described embodiment. FIG. 9 illustrates the scano data process in the third embodiment of the present invention.

In the above-described first and second embodiments, to obtain the scanogram, the output data from all the X-ray detector elements of the X-ray detector (two-dimensional array-like detector) is used. However, X-rays detected near the end of the slice thickness direction (the body axial direction) of the X-ray detector 12 are transmitted at a large angle to the subject P (that is, RC line), so the scanogram made by using the projection data according to that transmitted X-ray has an increased distortion. A slippage arising between the position in the scanogram and the position in the actual subject P is generated.

Accordingly, in the present embodiment, the scanogram is made only using the X-ray transmitting data transmitted almost perpendicularly to the subject P (RC line). That is, a plurality of rows (for example, 4 rows) of the X-ray detector elements, near the center in the slice thickness direction of the X-ray detector 12, necessary for generating the scanogram of the pre-set slice width, are selected. The scanogram is generated using only the data obtained from these rows.

In FIG. 9, 4 rows of the X-ray detector elements sandwiching the center in the slice thickness direction (the body axial direction) of the X-ray detector 12 are shown by slanting lines. The procedure of the scano data process in this case is the same as in the above-described first embodiment. Initially, the first scano data processing is conducted at a certain position of the subject P and after the data in the range of S1 (4 slices) on the rotation central axis RC of the X-ray tube 11 and the X-ray detector 12 is obtained. The next scano data processing is conducted by moving the top board 5 by the row width K of the X-ray detector 12. Then, the data in the next range S2 (4 slices) is obtained. In the same manner, the scano data up to the range Sn is obtained.

Also in this case, in the same manner as the first embodiment, because the subject P is successively moved by a distance equivalent to all of the X-ray element rows arranged in the slice thickness direction of the X-ray detector 12 (that is, the width K of the X-ray detector 12) every X-ray irradiation between the obtained data (between Sn-1 and Sn), a portion over which the X-ray beam does not cover, is produced. Because the data in this portion does not exist, the data is filled up, for example, by interpolation using the before and after data. In this manner, the scanogram in the desired range is made. The flow of the scanogram generation according to thus obtained data is also the same as in the first embodiment.

Further, the relationship between the position information of the top board 5 and the trigger signal of the X-ray irradiation from the X-ray tube 11 is shown in FIG. 6. The scano data processing in the desired range may also be conducted by intermittently irradiating the X-ray, every time when the top board 5 is moved by a distance corresponding to X-ray element rows arranged in the slice thickness direction of the X-ray detector 12. Alternatively, the scano data processing may be conducted while the top board 5 is continuously slid. Thus, every time when the top board 5 is moved by the distance corresponding to all of the X-ray element rows arranged in the slice thickness direction of the X-ray detector 12, the trigger signal may be generated and the X-ray may also be irradiated.

In the case of the present embodiment, only one portion in the array of the X-ray detector elements in the slice thickness direction is used for acquiring the scano data, so the range of the scanogram which can be made by one time X-ray irradiation is narrower as compared with that of the above-described first and second embodiments. Therefore, a period of the time of the scano data process is extended. However, only the detection data according to the X-ray in which the x-ray beam transmits to the subject P almost perpendicularly is used to make the scanogram. In this manner, small strain (high resolution) and accurate scanograms can be made in a short time. Furthermore, the array of the X-ray detector elements (the X-ray detector element rows) necessary for generating the scanogram of the pre-set plurality of slices are selected and the scano data processing is conducted. The scanogram is generated by using the data of the selected array of X-ray detector elements (the selected X-ray detector element rows). Therefore, the resolution of the generated scanogram is better than the conventional scanogram.

Figure 10:
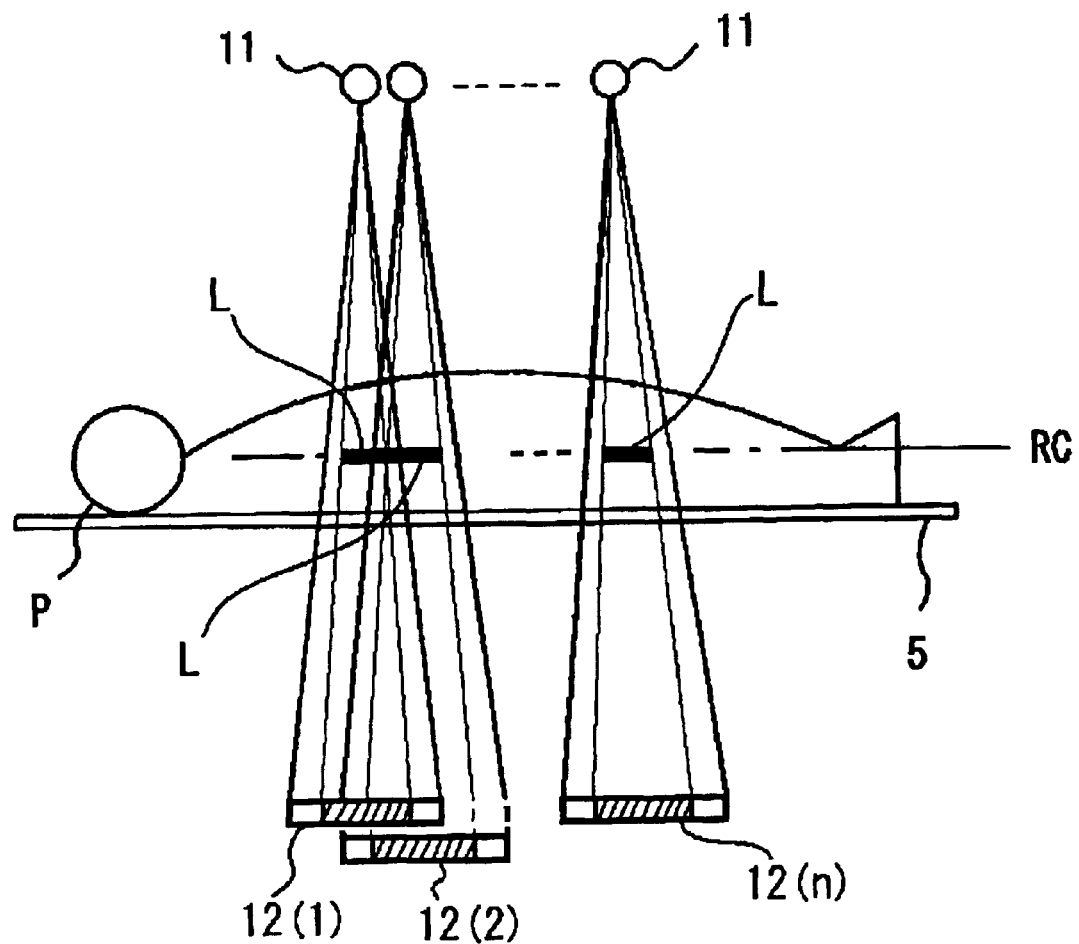
FIG. 10 is a schematic illustration of the scano data process in the fourth embodiment of the present invention.

Next, a fourth embodiment of the present invention will be described with reference to FIG. 10. FIG. 10 is a view for explaining the scano data process in the fourth embodiment of the present invention. The structure of the X-ray CT apparatus according to the fourth embodiment is the same as in the third embodiment. The difference between the fourth embodiment and the third embodiment is similar to the difference between the first embodiment and the second embodiment. In the fourth embodiment, although the slide pitch of the top board which is moved at every time of scano data process, it is a little smaller as compared with the third embodiment. Thus, when the scanogram is made, the method such as interpolation to fill up the lack of the data is not necessary in the fourth embodiment.

For example, as shown in FIG. 10, the top board 5 is slid the distance of X-ray beam width L (4 slices) on the rotation central axis RC of the X-ray tube 11 and the X-ray detector 12 at every scano data process (every X-ray beam is into contact with each other) and the scano data processing is conducted. The width L is the X-ray beam width on RC such that the X-ray beam transmitted the subject P is detected in 4 rows (slanting line portion) sandwiching the center in the slice thickness direction of the array of X-ray detector elements of the X-ray detector 12 exactly.

Also in the present embodiment, the relationship between the position information of the top board 5 and the trigger signal of the X-ray irradiation from the X-ray tube 11 is the same as in FIG. 6, and the scano data processing in the desired range may also be conducted by intermittently irradiating the X-ray every when the top board 5 is moved by the width L, or while the top board 5 is continuously slid, the trigger signal is generated every time when the top board 5 is moved by the row width L, the X-ray is irradiated.

In this case, it is preferable that the movement speed of the top board 5 is set to the optimum speed corresponding to the pulse width of the irradiated X-ray. That is, when V satisfying the above-described expression (1) is set as the optimum movement speed of the top board 5, the overlap of the scanogram is reduced. Accordingly, useless X-ray irradiation can be suppressed. Further, the scanogram is made by using only the detection data according to the X-ray in which the X-ray beam is transmitted almost perpendicularly to the subject P, and the scano data in the desired range can be acquired so the compensation (such as the interpolation) is not necessary at the time of the re-construction of the scanogram. Accordingly, the small strain and very high accurate scanogram can be made in a comparatively short time. Further, the array of the X-ray detector elements (the X-ray detector element rows) necessary for generating the scanogram of the pre-set plurality of slices are selected and the scano data processing is conducted, and the scanogram is generated by using the data of the selected array of X-ray detector elements (the selected X-ray detector element rows). Therefore, the resolution of the generated scanogram is better than the conventional scanogram.

Next, a fifth embodiment of the present invention will be described with reference to FIG. 11, which illustrates schematically the scano data process in the fifth embodiment of the present invention. In the above-described other embodiments, the control of the width of the X-ray beam in the slice thickness direction (the body axial direction) is not considered. Particularly, in the third and fourth embodiments, at the time of the scano data process, the data detected by the X-ray detector element of the outside of 4 rows sandwiching the center in the body axial direction of the X-ray detector 12 is not used for the scanogram generation.

In the fifth embodiment, at the time of the scano data process, the collimator in the gantry 1 is controlled corresponding to the number of the X-ray detector elements in the body axial direction of the X-ray detector 12 which acquires the data for the scanogram generation, and the width of the X-ray beam in the slice thickness direction (body axial direction) of the X-ray beam is stopped down. The X-ray is made to be hardly detected in the array of the X-ray detector elements except the array of the X-ray detector elements for the scano data acquisition.

Figure 11:
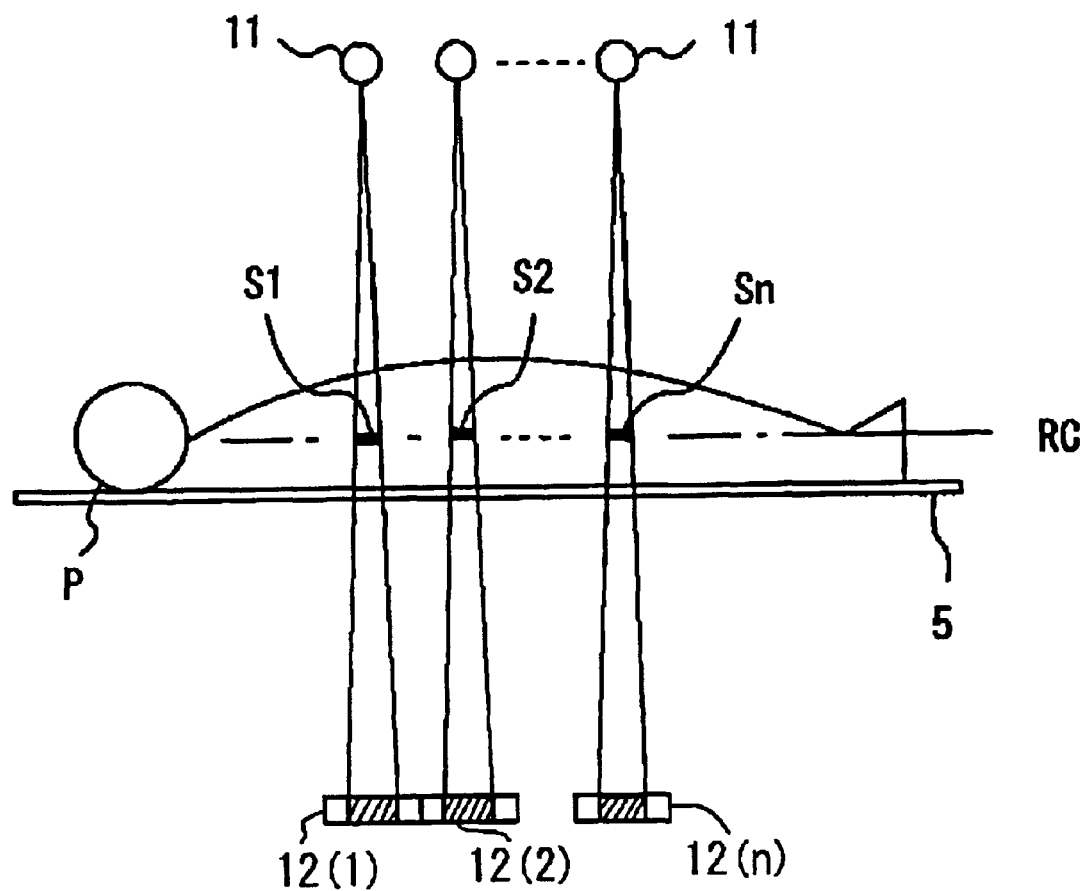
FIG. 11 is a schematic illustration of the scano data process in the fifth embodiment of the present invention.

For example, as shown in FIG. 11, corresponding to the pre-set slice width, 4 rows (between the slanting lines) sandwiching the center of the X-ray detector of the number of the X-ray detector elements in the body axial direction of the X-ray detector 12 which acquires the scano data at the time of the scano data process are selected. Then, corresponding to that number of rows, the stop (collimator) is operated, and the beam width in the slice thickness direction of the X-ray beam irradiated from the irradiation aperture of the gantry 1 is stopped down by the stop. This control procedure of the stop is performed as follows. For example, the operator designates the scano data process mode by the input unit 6. Then, the CPU 21 determines the stop amount of the X-ray beam so that the width of the X-ray beam on the rotation central axis RC is nearly equal to the pre-set slice width. According to the determined stop amount, the control unit 20 controls the stop.

After the control of the stop is completed, the scano data processing is started. The procedure of the scano data process is the same as the third embodiment. That is, initially, the first scano data processing is conducted at a certain position of the subject P. After the data of the range of S1 (for 4 slices) on the rotation central axis RC of the X-ray tube 111 and the X-ray detector 12 is obtained, the next scano data processing is conducted by moving the top board 5 by the row width K of the X-ray detector 12. Then, the scano data in the next range S2 is obtained. In the same manner, the data up to the range Sn is obtained.

In this case, the X-ray beam does not reach between the obtained data S1 to Sn, so the data does not exist in these portions. Therefore, by using the data obtained before and after, the data is filled by processing, such as by interpolation. In this manner, the scanogram in the desired range is generated by re-constructing the obtained data.

In this situation, also in the present embodiment, the relationship between the position information of the top board 5 and the trigger signal of the X-ray irradiation from the X-ray tube 11 is the same in FIG. 6. The scano data process in the desired range may also be conducted by intermittently irradiating the X-ray every time when the top board 5 is moved by the distance which totaled all of the X-ray element rows arranged in the slice thickness direction of the X-ray detector 12 (that is, the width K). Alternatively, while the top board 5 is continuously slid, the trigger signal is generated and the X-ray may also be irradiated every time when the top board 5 is moved by the distance K. For other than that, while the top board or the gantry is continuously moved, and the X-ray is continuously irradiated, the scano data processing may be conducted. Because the irradiation range of the X-ray is narrowed to the necessary minimum in the beginning, the scano data processing can be conducted in a short time while the X-ray is effectively used (that is, while excessive X-ray exposure to the subject is suppressed).

Conventionally, the control of the stop of the width of the X-ray beam in the body axial direction is not considered. However, according to embodiments of the present invention, the width of the X-ray beam in the body axial direction can be controlled corresponding to the number of the X-ray detector elements in the body axial direction of the X-ray detector 12 which acquires the data for generating the scanogram. In this way, the X-ray can be effectively used, and the scanogram can be obtained without excessive X-ray exposure to the subject. Further, the scanogram is made by using only the detection data acquired with the X-ray beam almost perpendicularly transmits to the subject P, so the small strain and highly accurate scanogram can be generated in a short time. Further, the array of the X-ray detector elements (the X-ray detector element rows) necessary for generating the scanogram of the pre-set plurality of slices are selected and the scano data processing is conducted, and the scanogram is generated by using the data of the selected array of X-ray detector elements (the selected X-ray detector element rows). Therefore, the resolution of the generated scanogram is better than the conventional scanogram.

Next, a scano data process of a sixth embodiment of the present invention will be described with reference to FIG. 12.

In the above fifth embodiment, missing data is filled in by the process such as the interpolation. However, in the present sixth embodiment, the movement of the top board 5 is controlled so that the missing data is not caused.

Figure 12:
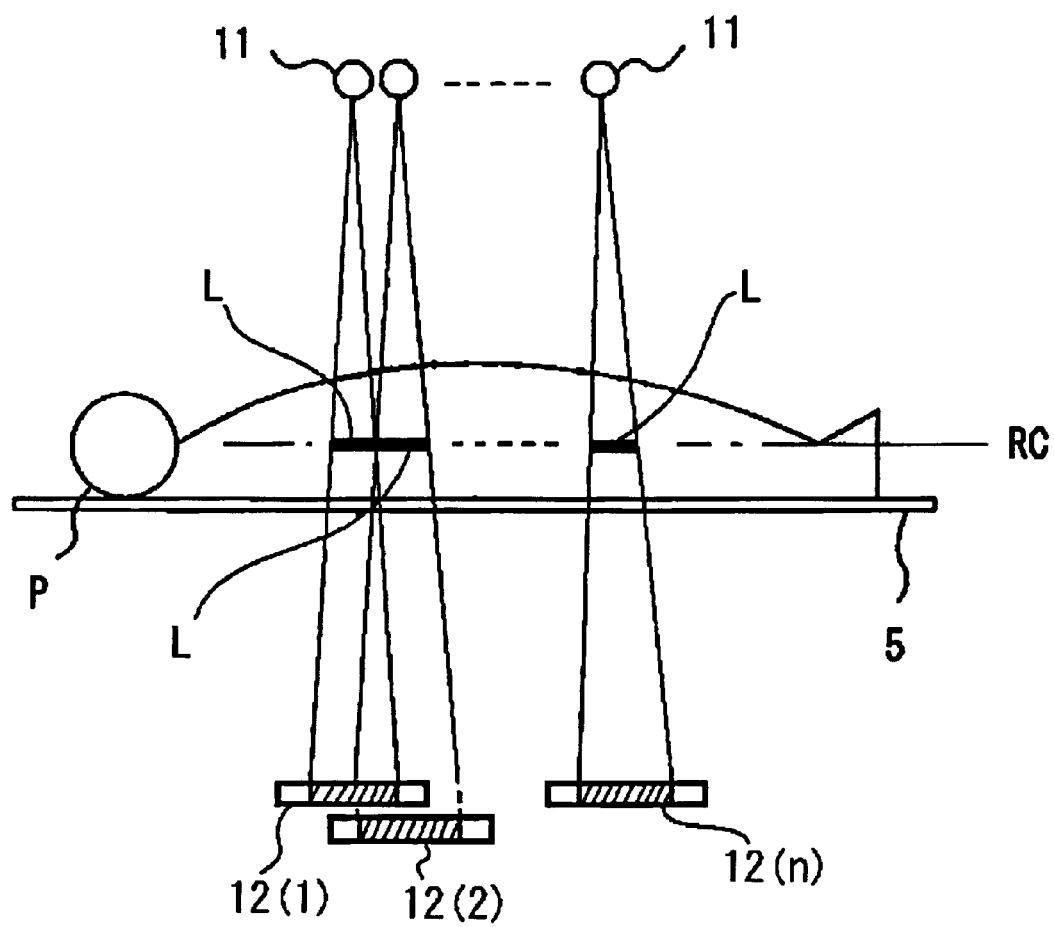
FIG. 12 is a schematic illustration of the scano data process in the sixth embodiment of the present invention.

For example, as shown in FIG. 12, corresponding to the previously set slice width, 4 rows (slanting line portion) are selected sandwiching the center of X-ray detector element rows in the body axial direction of the X-ray detector 12 acquiring the data at the time of scano data process. Then, the stop is moved corresponding to the number of the rows, and the beam width in the slice thickness direction of the X-ray beam irradiated from the irradiation aperture of the gantry 1 is narrowed. The control method of the stop is the same as in the fifth embodiment.

After the control of the stop is completed, the scano data processing is started. The procedure of the scano data processing is the same as in the fourth embodiment. That is, the top board 5 is slid the distance of X-ray beam width L (4 slices) on the rotation central axis RC of the X-ray tube 11 and the X-ray detector 12 at every scano data process (every X-ray beam is into contact with each other) and the scano data processing is conducted. The width L is the X-ray beam width on RC such that the X-ray beam transmitted the subject P is detected in 4 rows (slanting line portion) sandwiching the center in the slice thickness direction of the array of X-ray detector elements of the X-ray detector 12 exactly. That is, because the data width on the RC corresponds to the slice width, the top board 5 is slid by the set slice width, and the scano data processing may be conducted. In this manner, the projection data in the desired range is acquired, the acquired data is re-constructed, and the scanogram is generated.

In this situation, also in the present embodiment, the relationship between the position information of the top board 5 and the trigger signal of the X-ray irradiation from the X-ray tube 11 is the same as FIG. 6. The scano data process in the desired range may also be conducted by intermittently irradiating the X-ray every time when the top board 5 is moved by the distance equivalent to the width L of X-ray beam (4 slices). Alternatively, while the top board 5 is continuously slid, the trigger signal is generated and the X-ray may be also be irradiated every time when the top board 5 is moved by the distance L. Otherwise, while the top board or the gantry is continuously moved, the X-ray is continuously irradiated, and the scano data processing may also be conducted. Because the irradiation range of the X-ray is narrowed to the necessary minimum in the beginning, the scano data processing can be conducted in a short time while the X-ray is effectively used (that is, while excessive X-ray exposure to the subject is suppressed).

Further, it is preferable that the movement speed of the top board 5 is set to the optimum speed corresponding to the pulse width of the irradiated X-ray. That is, V satisfying the above-described expression (1) is set as the optimum movement speed of the top board 5, so the overlap of the scanogram is reduced. Accordingly, useless X-ray irradiation can be suppressed.

Further, only the detection acquired with the X-ray beam almost perpendicularly transmitted to the subject P is used to make the scanogram, and together with that, the projection data in the desired range can be acquired so compensation (such by interpolation) is not necessary when reconstructing the scanogram. Accordingly, the small strain and very highly accurate scanogram can be made in a comparatively short time.

Further, in the present embodiment, the array of the X-ray detector elements (the X-ray detector element rows) necessary for generating the scanogram of the pre-set plurality of slices are selected and the scano data processing is conducted. The scanogram is generated by using the data of the selected array of X-ray detector elements (the selected X-ray detector element row). Therefore, the resolution of the generated scanogram is better than the conventional scanogram.

In each of the above embodiments, the array of the X-ray detector elements necessary for generating the scanogram of the pre-set plurality of slice is selected, and the scano data processing is conducted, and the scanogram is generated by using the data of the selected array of the X-ray detector elements (the selected X-ray detector element row). Therefore, the speed of imaging a scanogram and resolution of the scanogram are improved as compared with the conventional one. However, S/N is not so good as compared with the conventional one. In order to obtain the same degree S/N as the conventional one, it is necessary to increase the quantity of the X-rays to be irradiated. However, to increase the quantity of the X-rays results in an undesirable increase the exposure of the subject to the X-ray.

Accordingly, instead of increasing the quantity of the X-ray, the following method can be used to increase the S/N instead. That is, the X-rays are irradiated from the X-ray tube every time when the top board or gantry (X-ray tube and X-ray detector) is moved by the distance of one row or a plurality rows of the X-ray detector elements in the slice thickness direction. The data of the position of the body axial direction acquired in the different time (that is, the overlapped data at the same position in the slice thickness direction) are processed by the addition average, and the data are used as the data of that position. By generating the scanogram according to thus obtained scano data, the S/N of the scanogram can be increased. To move the gantry, for example, a caster is provided on the lower portion of the gantry. When the movement amount by the caster is detected by detector, the detector detects that the gantry is moved by a predetermined movement amount, a signal is sent to the high-voltage generator 16, and the irradiation of the X-rays from the X-ray tube is conducted.

In this situation, FIG. 5, FIG. 7, FIG. 9, FIG. 10, FIG. 11, and FIG. 12 show that the X-ray tube 11 and the X-ray detector 12 are moved relative to the stationary subject P. However, this is relative, and of course, it is also the same when the top board is moved relative to the stationary X-ray tube 11 and X-ray detector 12.

The present invention is not limited to the above-described embodiments, but it can be conducted in the various modes.

For example, in FIG. 3, the uniform pitch X-ray detector 12 in which the X-ray detector elements of 40 rows in 1 mm pitch in the slice thickness direction are arrayed is shown. However, the pitch in the slice thickness direction is not necessarily a uniform pitch. For example, a non-uniform pitch X-ray detector can be structured by arraying the X-ray detector elements in a total 40 rows in which the central portion of 16 rows has 0.5 mm pitch while 12 rows on either side of the control portion have 1 mm pitch. In the embodiments of present invention, such an X-ray detector can also be used. Of course, the X-ray detector elements are not limited to 40 rows and the pitch is not limited to 0.5 mm or 1 mm. In this situation, herein, the value of the pitch of the X-ray detector elements is a value in the felt region to the X-ray in the rotation center (RC) of the X-ray tube 11 and the X-ray detector 12, and is not the actual dimension in the X-ray detector 12.

Further, in FIG. 8, it is described that the X-ray detector elements of the X-ray detector 12 are switched every 4 rows by the multiplexer 40, and the signal is supplied to DAS 17. However, when the method by which the X-ray detector elements are bundled for each channel, by the amount of 2 rows (more than that is allowed) in the slice thickness direction, and the signal is supplied to the DAS 17, is used in combination, the number of the DAS's 17 can be reduced in half. In this situation, the technology by which the signals from the array of the X-ray detector elements are bundled and supplied to the DAS, is detailed in, for example, Japanese Patent Disclosure (Kokai) 10-24031, which is incorporated by reference herein.

Further, in the above-described embodiments, an example is shown in which the X-ray detector elements for the amount of 4 rows from the center of the X-ray detector are used for the data acquisition for generating the scanogram. However, when the X-ray detector elements for acquiring the data are expanded from 4 rows, for example, to 16 rows, and the data detected by the X-ray detector elements near the outside is processed by the fan beam reconstruction to generate the scanogram, the imaging time can be reduced. This is because the strain of the scanogram at the position in the vicinity of the outside can be compensated, and the scanogram with the good accuracy can be more widely obtained by one time scano data processing.

As detailed above, according to embodiments of the present invention, a wide range of the scanogram can be obtained in a short time, the burden to the subject is lightened, and the patient throughputs can also be increased.

Various modifications and variations of the above embodiments can be made without departing from the novel and advantageous features of the present invention. Accordingly, all such modifications and variation are intended to be included within the scope of the invention.

What is claimed is:

1. An X-ray CT apparatus comprising:

an X-ray tube for generating X-rays;

an X-ray detector having a plurality of rows of X-ray detector elements arrayed in a slice thickness direction for detecting X-rays transmitted through a subject;

a selector configured to select the rows of the X-ray detector elements in the slice thickness direction necessary for generating a scanogram for a pre-set slice width; and a scanogram processing unit configured to generate the scanogram by using data detected by the row of X-ray detector elements selected by the selector;

a couch provided with a top board for placing the subject;

a moving device configured to move at least of the X-ray tube and X-ray detector and the top board in the slice thickness direction; and an X-ray irradiation controller configured to control an irradiation timing of the X-rays from the X-ray tube; and said X-ray irradiation controller configured to control irradiation timing so that the X-rays are irradiated every time when the at least one of the X-ray tube, X-ray detector and the top board are moved for the pre-set slice widths by the moving device;

a supporting device configured to support the X-ray tube and X-ray detector rotatably around the subject;

wherein the x-ray irradiation control unit is configured to control the irradiation timing of the X-rays so that X-ray beam at the time of the first X-ray irradiation and a X-ray beam at the time of the second X-ray irradiation on a rotation central axis of the X-ray tube and the X-ray detector are mutually touching.

2. An X-ray CT apparatus according to claim 1, wherein the X-ray irradiation control unit is configured to control the irradiation timing of the X-rays of the X-ray tube so that the X-rays are irradiated every time when the X-ray detector is moved by an amount of a row width in the body axial direction of the X-ray detector.

3. An X-ray CT apparatus according to claim 1, wherein the selector is configured to select a group of the rows of the X-ray detector elements near the center in the slice thickness direction of the X-ray detector.

4. An X-ray CT apparatus according to claim 1, wherein the scanogram processing unit is configured to generate the scanogram by using the first data obtained by the irradiation of a first group of the X-rays, second data obtained by the irradiation of a second group of the X-rays, and data interpolated between the first data and the second data.

5. An X-ray CT apparatus according to claim 1, further comprising:
   a data acquisition unit configured to acquire an output signal from the X-ray detector; and
   a multiplexer provided for the rows of X-ray detector elements in the slide thickness direction in the X-ray detector;
   wherein the data acquisition unit is connected through the multiplexer, and the output signal is acquired by switching the connection of the multiplexer between each row of X-ray detector elements.

6. An X-ray CT apparatus according to claim 1, wherein the moving device is configured to move the at least one of the X-ray tube, X-ray detector, and the top board in the slice thickness direction continuously.

7. An X-ray CT apparatus according to claim 1, further comprising:
   an X-ray stop device configured to control the beam width of the X-rays irradiated in the slice thickness direction according to the pre-set slice width.

8. An X-ray CT apparatus according to claim 7, wherein the X-ray stop device is configured to control the beam width so that the beam width of the X-ray on the rotation central axis of the X-ray tube and the X-ray detector are substantially equal to the pre-set slice width.

9. A method of X-ray CT imaging, comprising:
   supporting an x-ray tube and an X-ray detector rotatably around a subject;
   irradiating X-rays using an X-ray tube;
   detecting the X-rays transmitted through a subject using an X-ray detector having a plurality of rows of X-ray detector elements arrayed in a slice thickness direction;
   moving at least one of the X-ray tube and X-ray detector and a top board in the slice thickness direction;
   selecting at least one row of the X-ray detector elements in the slice thickness direction necessary for generating a scanogram for a pre-set slice width;
   generating the scanogram by using data detected by the selected at least one row of X-ray detector elements selected; and
   controlling an irradiation timing of X-rays from the X-ray tube so that the X-rays are irradiated every time when the at least one the X-ray tube and X-ray detector and the top board is move for the pre-set slice widths, comprising controlling the irradiation timing of the X-rays so that an X-ray beam at the time of a X-ray irradiation and an X-ray beam at the time of a second X-ray irradiation on a rotation central axis of the X-ray tube and the X-ray detector are mutually touching.

10. A method of X-ray CT imaging according to claim 9, wherein the moving step comprises:
    moving at least one of the X-ray tube and X-ray detector, and the top board in the slice thickness direction continuously.

11. A method of X-ray CT imaging according to claim 9, further comprising:
    stopping the beam width of the X-rays irradiated in the slice thickness direction according to the pre-set slice width.

12. A method of X-ray CT imaging according to claim 11, wherein the stopping step comprises:
    stopping the beam width so that the beam width of the X-ray on the rotation central axis of the X-ray tube and the X-ray detector are substantially equal to the pre-set slice width.

13. A method of X-ray CT imaging according to claim 9, wherein the selecting step comprises:
    selecting a group of the rows of the X-ray detector elements near a center in the slice thickness direction of the X-ray detector.

14. A method of X-ray CT imaging according to claim 9, wherein the generating step comprises:
    generating the scanogram by using first data obtained by the irradiation of a first group of the X-rays, second data obtained by the irradiation of a second group of the X-rays, and data interpolated between the first data and the second data.

15. A method of X-ray CT imaging according to claim 9, further comprising:
    acquiring an output signal from the X-ray detector, including
    connecting the data acquisition means with a multiplexer provided for the rows of X-ray detector elements in the slice thickness direction in the X-ray detector, and
    acquiring the output signal by switching the connection of the multiplexer between each row of X-ray detector elements.

16. A method of X-ray CT imaging according to claim 1, wherein the controlling step comprises:
    controlling the irradiation timing of the X-rays of the X-ray tube so that the X-rays are irradiated every time when the X-ray detector is moved by an amount of the row width in the body axial direction of the X-ray detector.

* * * * *